US009505691B2

(12) United States Patent
Shaver

(10) Patent No.: US 9,505,691 B2
(45) Date of Patent: Nov. 29, 2016

(54) PROCESS FOR PRODUCING ACETIC ACID

(71) Applicant: Celanese International Corporation, Dallas, TX (US)

(72) Inventor: Ronald David Shaver, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 0 days.

(21) Appl. No.: 14/874,369

(22) Filed: Oct. 2, 2015

(65) Prior Publication Data
US 2016/0102036 A1  Apr. 14, 2016

Related U.S. Application Data

(60) Provisional application No. 62/058,936, filed on Oct. 2, 2014.

(51) Int. Cl.
C07C 51/12 (2006.01)
C07C 51/09 (2006.01)
C07C 51/00 (2006.01)
C07C 51/44 (2006.01)

(52) U.S. Cl.
CPC ............ C07C 51/09 (2013.01); C07C 51/00 (2013.01); C07C 51/12 (2013.01); C07C 51/44 (2013.01)

(58) Field of Classification Search
CPC ..... A01B 12/006; C07C 51/09; C07C 51/12; C07C 51/00; C07C 53/08; C07C 51/44
See application file for complete search history.

(56) References Cited

U.S. PATENT DOCUMENTS

| | | | |
|---|---|---|---|
| 3,769,329 A | 10/1973 | Paulik et al. | |
| 3,772,156 A | 11/1973 | Johnson et al. | |
| 3,791,935 A | 2/1974 | Eubanks et al. | |
| 4,039,395 A | 8/1977 | Eby | |
| 4,139,688 A | 2/1979 | Dixon | |
| 4,255,591 A | 3/1981 | Makin et al. | |
| 4,615,806 A | 10/1986 | Hilton | |
| 4,786,699 A | 11/1988 | Nuber et al. | |
| 4,994,608 A | 2/1991 | Torrence et al. | |
| 5,001,259 A | 3/1991 | Smith et al. | |
| 5,026,908 A | 6/1991 | Smith et al. | |
| 5,139,981 A | 8/1992 | Kurland | |
| 5,144,068 A * | 9/1992 | Smith ............. C07C 51/12 203/77 |
| 5,220,058 A | 6/1993 | Fish et al. | |
| 5,227,520 A | 7/1993 | Cooper | |
| 5,227,524 A | 7/1993 | Jones | |
| 5,237,097 A | 8/1993 | Smith et al. | |
| 5,286,826 A | 2/1994 | Shih et al. | |
| 5,334,755 A | 8/1994 | Yoneda et al. | |
| 5,391,821 A | 2/1995 | Koyama et al. | |
| 5,416,237 A | 5/1995 | Aubigne et al. | |
| 5,466,874 A | 11/1995 | Scates et al. | |
| 5,625,095 A | 4/1997 | Miura et al. | |
| 5,653,853 A | 8/1997 | Kagotani et al. | |
| 5,672,744 A | 9/1997 | Kagotani et al. | |
| 5,683,492 A | 11/1997 | Hesse et al. | |
| 5,696,284 A | 12/1997 | Baker et al. | |
| 5,723,660 A | 3/1998 | Morimoto et al. | |
| 5,731,252 A | 3/1998 | Warner et al. | |
| 5,801,279 A | 9/1998 | Miura et al. | |
| 5,831,120 A | 11/1998 | Watson et al. | |
| 5,877,347 A | 3/1999 | Ditzel et al. | |
| 5,877,348 A | 3/1999 | Ditzel et al. | |
| 5,883,295 A | 3/1999 | Sunleu et al. | |
| 5,916,422 A | 6/1999 | Kimura et al. | |
| 5,932,764 A | 8/1999 | Morris et al. | |
| 5,942,460 A | 8/1999 | Garland et al. | |
| 5,962,735 A | 10/1999 | Kulprathipanja et al. | |
| 6,066,762 A | 5/2000 | Yoneda et al. | |
| 6,143,930 A | 11/2000 | Singh et al. | |
| 6,225,498 B1 | 5/2001 | Blay et al. | |
| 6,255,527 B1 | 7/2001 | Muskett | |
| 6,339,171 B1 | 1/2002 | Singh et al. | |
| 6,657,078 B2 | 12/2003 | Scates et al. | |
| 7,005,541 B2 | 2/2006 | Cheung et al. | |
| 7,208,624 B2 | 4/2007 | Scates et al. | |
| 7,223,883 B2 | 5/2007 | Picard et al. | |
| 7,223,886 B2 | 5/2007 | Scates et al. | |
| 7,271,293 B2 | 9/2007 | Trueba et al. | |
| 7,476,761 B2 | 1/2009 | Kojima | |

(Continued)

FOREIGN PATENT DOCUMENTS

CN  1349855 A    5/2002
CN  1562937   * 10/2003

(Continued)

OTHER PUBLICATIONS 937 translated 2016.*
"The Cativa .TM.Process for the Production of Acetic Acid", Chem. Ind. (Dekker) 1998, 75 Catalysis of Organic Reactions of Derrick J. Watson, pp. 369-380.
Akinori, S. "Acetic Acid Synthesis From Methanol" J. Japan Petroleum Institute 20(5); 379-462 (1977).
English translation of JP2000-72712.
English translation of Akinori, S. "Acetic Acid Synthesis From Methanol" J. Japan Petroleum Institute 20(5); 379-462 (1977).

(Continued)

Primary Examiner — Yevegeny Valenrod
Assistant Examiner — Blaine G Doletski
(74) Attorney, Agent, or Firm — Mark L. Cooper; Cooper & Assoc.

(57) ABSTRACT

Process for producing acetic acid is disclosed in which the reaction medium is separated into a liquid recycle and a vapor product stream including acetic acid, methyl iodide, methyl acetate and water in a flash vessel. The vapor product stream is condensed into a liquid stream that is enriched in acetic acid and this liquid stream is further sent to the distillation columns to recover acetic acid. The process advantageously improves the capacity of the acetic acid production while reducing the amount of acetic acid that is recycled.

17 Claims, 2 Drawing Sheets

(56) References Cited

U.S. PATENT DOCUMENTS

| | | |
|---|---|---|
| 7,678,940 B2 | 3/2010 | Miura et al. |
| 7,683,212 B2 | 3/2010 | Kojima et al. |
| 7,838,701 B2 | 11/2010 | Trueba et al. |
| 7,855,306 B2 | 12/2010 | Zinobile et al. |
| 7,884,237 B2 | 2/2011 | Shaver |
| 8,076,507 B2 | 12/2011 | Scates et al. |
| 8,173,076 B2 | 5/2012 | Powell et al. |
| 8,530,696 B2 | 9/2013 | Zinobile |
| 8,697,908 B2 | 4/2014 | Torrence et al. |
| 8,889,904 B2 | 11/2014 | Shaver et al. |
| 8,940,932 B2 | 1/2015 | Shimizu |
| 8,957,248 B2 | 2/2015 | Miura et al. |
| 2006/0011462 A1 | 1/2006 | Horiguchi et al. |
| 2006/0247466 A1 | 11/2006 | Zinobile et al. |
| 2009/0036710 A1 | 2/2009 | Miura et al. |
| 2009/0062525 A1 | 3/2009 | Shibata et al. |
| 2009/0259072 A1 | 10/2009 | Umehara et al. |
| 2011/0288333 A1 | 11/2011 | Shaver et al. |
| 2012/0078012 A1 | 3/2012 | Torrence et al. |
| 2012/0090981 A1 | 4/2012 | Torrence et al. |
| 2012/0132515 A1 | 5/2012 | Ohno |
| 2013/0026458 A1 | 1/2013 | Fukui et al. |
| 2013/0116470 A1* | 5/2013 | Miura .............. C07C 51/12 562/519 |
| 2013/0204014 A1 | 8/2013 | Nishihara et al. |
| 2013/0261334 A1 | 10/2013 | Shimizu et al. |
| 2013/0264186 A1 | 10/2013 | Shimizu et al. |
| 2013/0281735 A1 | 10/2013 | Shimizu et al. |
| 2015/0025270 A1* | 1/2015 | Shimizu .............. C07C 51/44 562/519 |
| 2015/0299084 A1 | 10/2015 | Shimizu et al. |

FOREIGN PATENT DOCUMENTS

| | | |
|---|---|---|
| CN | 1640843 A | 7/2005 |
| CN | 101053841 A | 10/2007 |
| EP | 0161874 A1 | 11/1985 |
| EP | 0685445 A1 | 12/1995 |
| EP | 1737808 B1 | 11/2006 |
| JP | 2000-72712 A | 3/2000 |
| WO | 9822420 A1 | 5/1998 |
| WO | 0216297 A1 | 2/2002 |
| WO | 2005085166 A1 | 11/2006 |
| WO | 2013137236 A1 | 9/2013 |
| WO | WO2013137236 * | 9/2013 |
| WO | 2014097867 A1 | 6/2014 |

OTHER PUBLICATIONS

Written Opinion of the International Searching Authority PCT/US2015/053886 Mailed Jan. 25, 2015.

International Search Report PCT/US2015/053886 Mailed Jan. 25, 2015.

* cited by examiner

PROCESS FOR PRODUCING ACETIC ACID

RELATED APPLICATION

This application claims priority to U.S. Provisional Application Ser. No. 62/058,936 filed Oct. 2, 2014, the disclosure of which is fully incorporated herein by reference

BACKGROUND

Among currently employed processes for synthesizing acetic acid, one of the most useful commercially is the catalyzed carbonylation of methanol with carbon monoxide as taught in U.S. Pat. No. 3,769,329, which is incorporated herein by reference in their entirety. The carbonylation catalyst contains a metal catalyst, such as rhodium, which is either dissolved or otherwise dispersed in a liquid reaction medium or supported on an inert solid, along with a halogen-containing catalyst promoter as exemplified by methyl iodide. Most typically and usefully, the reaction is conducted by continuously bubbling carbon monoxide gas through a liquid reaction medium in which the catalyst is dissolved.

Methanol and carbon monoxide are fed to a reactor as feedstocks. A portion of the reaction medium is continuously withdrawn and provided to a flasher where the product is flashed and sent as a vapor to a purification train. The purification train includes a light ends column which removes "light" or low boiling components as an overhead and provides a side stream for further purification. The purification train may further include columns to dehydrate the side stream or for removing "heavy" or high boiling components, such as propionic acid, from the side stream. It is desirable in a carbonylation process for making acetic acid to minimize the number of distillation operations to minimize energy usage in the process. U.S. Pat. No. 5,416,237 discloses a process for the production of acetic acid by carbonylation of methanol in the presence of a rhodium catalyst, methyl iodide, and an iodide salt stabilizer. The improvement according to the '237 patent resides in maintaining a finite concentration of water up to about 10 wt. % and a methyl acetate concentration of at least 2 wt. % in the liquid reaction composition and recovering the acetic acid product by passing the liquid reaction composition through a flash zone to produce a vapor fraction which is passed to a single distillation column from which the acetic acid product is removed. The drawback of eliminating distillation stages is that the level of purity of the product suffers. In particular, the distillation columns tend to remove high boiling iodides as well as aldehyde contamination products. Both of these impurities impact the commercial desirability of the final product.

U.S. Pat. No. 6,657,078 discloses a low energy process for producing acetic acid by the carbonylation of methanol. The process involves a rhodium-catalyzed system operated at less than about 14 wt. % water utilizing up to 2 distillation columns.

US Pub. No. 2013/0116470 discloses a production process of acetic acid comprises a reaction step for continuously allowing at least one member selected from the group consisting of methanol, dimethyl ether, and methyl acetate to react with carbon monoxide in a catalyst system comprising a rhodium catalyst, an iodide salt, and methyl iodide in the presence of acetic acid and water in a plant compromising a reactor, a flasher, and a distillation column, and wherein part of the vaporized stream is introduced into a heat exchanger. The liquid portion that is condensed from the vaporized stream is returned to the reactor for cooling purposes. As a result of a need to cool the reactor, the process disclosed in US Pub. No. 2013/0116470 increases the recycle of acetic acid which reduces carbon monoxide efficiency.

A frequent production limitation in the purification section of an acetic acid unit is the light ends column. In a typical acetic acid methanol carbonylation process, hot high pressure liquid from the reactor is reduced in pressure across a valve and flashed in a lower pressure flasher vessel. The vapors liberated from this step are fed near the bottom of a light ends column. Condensed liquids rich in acetic acid are removed from a liquid sidedraw above the feed and fed forward for further purification, while vapors exiting the tower overhead are condensed and fed to a liquid-liquid decanter. The light phase from the decanter is refluxed to the tower and the heavy phase is recycled to the reactor feed. Thus, the light ends column receives a hot vapor product stream from the flasher and operates to remove most of the methyl acetate and methyl iodide from the stream before the product stream is fed forward for water removal. U.S. Pat. No. 8,173,076 describes an improved apparatus and method of producing acetic acid which includes condensing overhead vapor to provide reflux to the light ends column as well as condensing vapor from a central portion of the light ends column to increase capacity.

Thus, what is needed is an improvement to an acetic acid production process that does not result in increased recycle of acetic acid and improves the operation of the light ends column.

SUMMARY

In a first embodiment the present invention relates to a process for the production of acetic acid comprising carbonylating at least one reactant selected from the group consisting of methanol, dimethyl ether, methyl acetate, and mixtures thereof, in the presence of 0.1 to 14 wt. % water, a metal catalyst, methyl iodide and iodide salt to form a reaction medium in a reactor, and separating the reaction medium into a liquid recycle and a vapor product stream including acetic acid, methyl iodide, methyl acetate and water. The process further comprises condensing a first portion of the vapor product stream, i.e. 1 to 50%, to form a liquid stream and a vapor stream; feeding a second portion of the vapor product stream, i.e. 50 to 99%, to a first column, feeding some or all of the liquid stream, preferably at least 10%, to the first column, and withdrawing a side stream comprising an acetic acid product from the first column. In one embodiment, the process comprises feeding the side stream to a second column to obtain an acetic acid purified product. Some of the liquid stream may be introduced into the second column. The liquid stream may be enriched in acetic acid compared to the second portion of the vapor stream and comprises from 65 to 95 wt. % acetic acid. In one embodiment, the liquid stream is not returned to the reactor and the reactor has a cooling unit, such as a pump around loop. The process of the present invention advantageously maintains carbon monoxide efficiency in the reactor is maintained above 90%.

In a second embodiment the present invention relates to a process for the production of acetic acid comprising carbonylating at least one reactant selected from the group consisting of methanol, dimethyl ether, methyl acetate, and mixtures thereof in the presence of 0.1 to 14 wt. % water, a metal catalyst, methyl iodide and iodide salt to form a reaction medium in a reactor, and separating the reaction medium into a liquid recycle and a vapor product stream including acetic acid, methyl iodide, methyl acetate and water in a flash vessel having an optional upper scrubbing section. The process further comprises condensing a first portion of the vapor product stream, e.g. 1 to 50%, to form a liquid product stream and a vapor stream, feeding a second portion of the vapor product stream, e.g. 50 to 99%, to a first column, withdrawing a side stream comprising an acetic acid product from the first column to a second column, feeding some or all of the liquid product stream, preferably at least 10%, to the second column, and obtaining an acetic acid purified product from the second column. In one embodiment, some of the liquid stream may be introduced into the first column. The liquid stream may be enriched in acetic acid and comprise from 65 to 95 wt. % acetic acid. In one embodiment, the liquid stream comprising an amount equal or more than the acetic acid in the side stream, e.g., more than 90%. In one embodiment, the liquid stream is not returned to the reactor and the reactor has a cooling unit, such as a pump around loop. The process of the present invention advantageously maintains carbon monoxide efficiency in the reactor is maintained above 90%.

BRIEF DESCRIPTION OF THE DRAWINGS

The present invention will be better understood in view of the appended non-limiting figures, wherein.

DETAILED DESCRIPTION

Introduction

Figure 1:
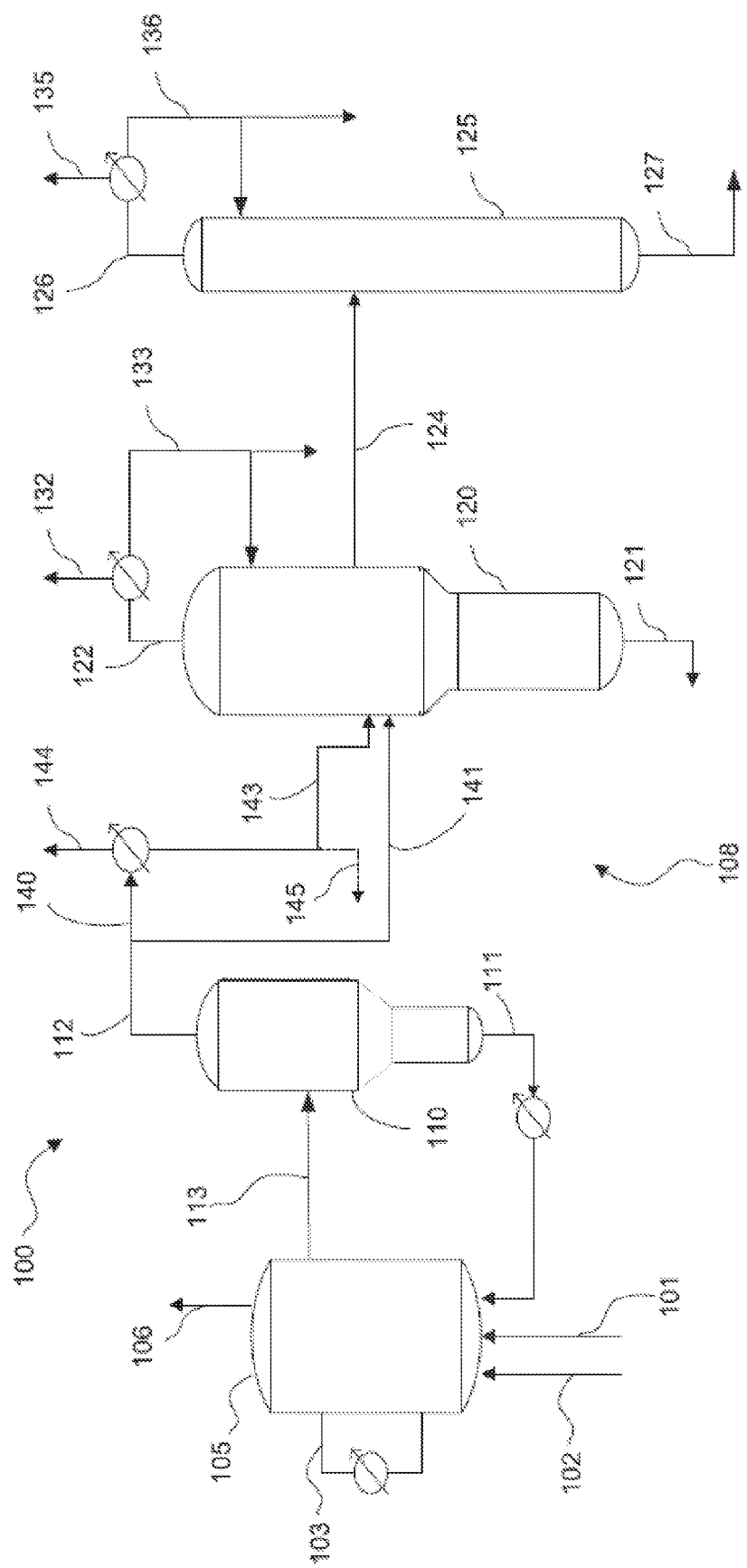
FIG. 1 is a schematic drawing of condensing vapor product stream to yield a liquid stream that is introduced to a first column in accordance embodiments of the process disclosed herein.

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein:
acetic acid may be abbreviated as "AcOH";
acetaldehyde may be abbreviated as "AcH";
methyl acetate may be abbreviated "MeAc";
methanol may be abbreviated "MeOH";
methyl iodide may be abbreviated as "MeI";
hydrogen iodide may be abbreviated as "HI";
carbon monoxide may be abbreviated "CO"; and
HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages", "flow paths", "flow conduits", and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

The instant disclosure is directed to processes for producing acetic acid and reducing the recycle of acetic acid to the reactor. The process provides a method for removing acetic acid from a condensed portion, i.e., liquid stream, of a vapor product stream prior to being returned to the reactor. The liquid stream is enriched in acetic acid compared to the vapor product stream and thus it is more advantageous to recover acetic acid by feeding some or all of the liquid stream to a first column and/or second column. In some embodiments, some of the liquid stream may be returned to the reactor. Advantageously, by introducing an enriched acetic acid liquid stream into the first column and/or second column, the operation of those columns may be improved. In particular, the first column may be debottlenecked without significantly changing the side stream composition.

In embodiments, the liquid stream from the condensed vapor product stream is fed to a first column. The process for producing acetic acid according to a first embodiment of the present invention comprises carbonylating at least one reactant selected from the group consisting of methanol, dimethyl ether, methyl acetate, and mixtures thereof, in the presence of 0.1 to 14 wt. % water, a metal catalyst, methyl iodide and iodide salt to form a reaction medium in a reactor; separating the reaction medium into a liquid recycle and a vapor product stream including acetic acid, methyl iodide, methyl acetate and water; condensing a first portion of the vapor product stream to form a liquid stream and a vapor stream; feeding a second portion of the vapor product stream to a first column; feeding some or all of the liquid stream to the first column; and withdrawing a side stream comprising an acetic acid product from the first column. Without being bound by theory the hydraulic load may be reduced in the first column above where the side stream is removed. Advantageously, this increases the production rates of the process.

In embodiments, the liquid stream from the condensed vapor product stream is fed to a second column, without passing through the first column. Thus, the load in the first column may be reduced and acetic acid may be recovered in the second column. The process for producing acetic acid according to embodiments comprises carbonylating at least one reactant selected from the group consisting of methanol, dimethyl ether, methyl acetate, and mixtures thereof in the presence of 0.1 to 14 wt. % water, a metal catalyst, methyl iodide and iodide salt to form a reaction medium in a reactor, separating the reaction medium into a liquid recycle and a vapor product stream including acetic acid, methyl iodide, methyl acetate and water in a flash vessel having an optional upper scrubbing section, condensing a first portion of the vapor product stream to form a liquid product stream and a vapor stream, feeding a second portion of the vapor product stream to a first column, withdrawing a side stream comprising an acetic acid product from the first column to a second column, feeding some or all of the liquid product stream to the second column, and obtaining an acetic acid purified product from the second column. Optionally, due to the entrainment of catalyst and other corrosion metals, the flasher may have a scrubber section. Advantageously, this increases the production rates of the process.

In other embodiments, there may be a combination of the first and second embodiment, and the liquid stream may be split and fed to both the first and second column. Preferably the amount of liquid stream that is split is larger than the amount of liquid stream, if any, that is recycled to the reactor.

The vapor product stream from the flasher comprises acetic acid, methyl iodide, methyl acetate, water, and other impurities such as acetaldehyde, crotonaldehyde, higher acetates, and organic iodides. The concentration of acetic acid in the vapor product stream may range from 30 to 70 wt. %, e.g., from 40 to 60 wt. %, or from 45 to 55 wt. %. The vapor product stream typically transfers the latent heat of the reaction to the first column to recover acetic acid in the side stream. The latent heat of the reaction may exceed the energy requirements of the first column, and thus embodiments according to the instant disclosure advantageously condenses a first portion of the vapor product stream to recover an acetic acid enriched liquid stream. The remaining portion of the vapor product, i.e., second portion, is introduced to the first column to further remove impurities and reaction medium components. The amount of the vapor product stream that is condensed may be an amount sufficient that does not impact the energy requirements of the first column. In condensing vapor product stream, the liquid stream may be enriched in acetic acid as compared to the vapor product stream. In one embodiment, the composition of acetic acid in the liquid stream relative to the composition of acetic acid in the vapor product stream is at least 5% enriched, e.g., at least 10% or at least 15%. The concentration of acetic acid in the liquid stream may be from 65 to 95 wt. % acetic acid, e.g., from 70 to 90 wt. % acetic acid or from 80 to 90 wt. % acetic acid.

The condensation of the liquid stream may remove reactant components and impurities in a vapor stream. The vapor stream may be sent to a scrubber or an impurity removal column to recover the reactant components, and in particular methyl iodide and methyl acetate. In other embodiments, the vapor stream or a portion thereof may be purged as needed.

Once cooled, at least 10% of the liquid stream may be fed to the first column and/or second column. In one preferred embodiment, at least 25%, e.g., at least 50%, at least 75% or at least 90%, of the liquid stream may be fed to the first column and/or second column. When introduced to the first column, the liquid stream may be introduced above the feed of the second portion of the vapor product stream and in some embodiments, above the side stream. When introduced to the second column, the liquid stream may be introduced with the side stream feed or in the upper portion of the second column. Although the location is not particularly limited, it is preferable that the liquid stream is introduced into the first and/or second column at a location that does not disrupt the column dynamics. As more of the liquid stream is fed forward to the first column and/or second, less acetic acid is recycled to the reactor. As described in US Pub. No. 2013/0116470, the liquid stream is fed to the reactor for cooling purposes. A disadvantage of this is that acetic acid is recycled and carbon monoxide efficiency is decreased because the recycle of the liquid stream leads to an increase flow of the stream from the reactor to the flasher which contains dissolved and entrained gases, primarily containing carbon monoxide. Dissolved and entrained gases are subsequently lost in the vents of the purification train. Also by returning a large liquid stream containing acetic acid, the liquid stream would need to be increased in pressure so that it may be fed to reactor. Recycling acetic acid increases the recycles to the reactor and additional pumping would be required which impacts both equipment and operation costs. This places further limitations on using the liquid stream as a coolant for the reactor. In an embodiment, all of the liquid stream is fed to either the first and/or second column and none of the liquid stream is returned to the reactor. In such an embodiment, the reactor may have a separate cooling system and does not require the input of the recycle steps to cool the reactor. By avoiding the necessity to recycle the liquid stream to the reactor, in embodiments, the process may maintain carbon monoxide efficiencies above 90%, defined as the amount of carbon monoxide feed that is converted to acetic acid.

Embodiments will now be described in detail by reference to the drawings. The embodiments shown in FIGS. 1 and 2 show a process for producing a purified acetic acid product from a liquid medium generated by a continuously carbonylation reaction of a methanol reactant in the presence of the metal catalyst, methyl iodide, water, and an iodide salt.

Reaction Step

Figure 2:
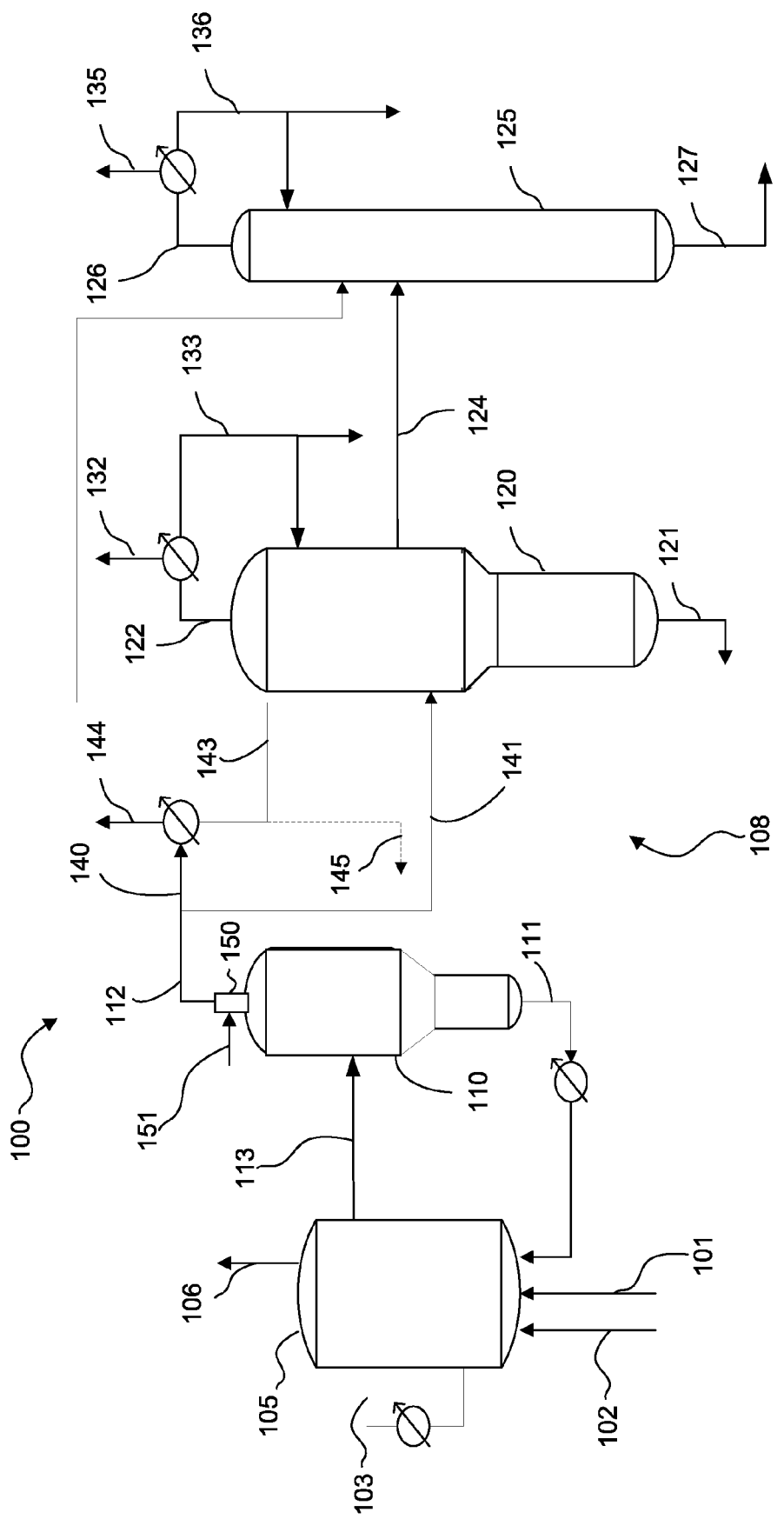
FIG. 2 is a schematic drawing of condensing vapor product stream to yield a liquid stream that is introduced to a second column in accordance with alternative embodiments disclosed herein.

Exemplary reaction and acetic acid recovery system 100 is shown in FIGS. 1 and 2. As shown, methanol-containing feed stream 101 and carbon monoxide-containing feed stream 102 are directed to liquid phase carbonylation reactor 105, in which the carbonylation reaction occurs to form acetic acid.

Methanol-containing feed stream 101 may comprise at least one member selected from the group consisting of methanol, dimethyl ether, and methyl acetate. Methanol-containing feed stream 101 may be derived in part from a fresh feed or may be recycled from the system. At least some of the methanol and/or reactive derivative thereof will be converted to, and hence present as, methyl acetate in the liquid medium by esterification reaction with acetic acid.

Typical reaction temperatures for carbonylation will be from 150 to 250° C., with the temperature range of 180 to 225° C. being a preferred range. The carbon monoxide partial pressure in the reactor may vary widely but is typically from 2 to 30 atm, e.g., from 3 to 10 atm. The hydrogen partial pressure in the reactor is typically from 0.05 to 2 atm, e.g., from 1 to 1.9 atm. Because of the partial pressure of by-products and the vapor pressure of the contained liquids, the total reactor pressure will range from 15 to 40 atm. The production rate of acetic acid may be from 5 to 50 mol/L·h, e.g., from 10 to 40 mol/L·h, and preferably about 15 to 35 mol/L·h.

Carbonylation reactor 105 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 105, fresh methanol, carbon monoxide, and sufficient water are continuously introduced as needed to maintain suitable concentrations in the reaction medium.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including $[Rh(CO)_2I_2]$-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144, 068 and 7,005,541, which are incorporated herein by reference in their entirety. The carbonylation of methanol utilizing iridium catalyst is well known and is generally described in U.S. Pat. Nos. 5,942,460, 5,932,764, 5,883,295, 5,877, 348, 5,877,347 and 5,696,284, which are incorporated herein by reference in their entirety.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter will include methyl halide, and more preferably methyl iodide.

The components of the reaction medium are maintained within defined limits to ensure sufficient production of acetic acid. The reaction medium contains a concentration of the metal catalyst, e.g. rhodium catalyst, in an amount from 200 to 3000 wppm, e.g., from 800 to 3000 wppm, or from 900 to 1500 wppm. The concentration of water in the reaction medium is maintained to be up to 14 wt. %, e.g., from 0.1 wt. % to 14 wt. %, from 0.2 wt. % to 10 wt. % or from 0.25 wt. % to 5 wt. %. Preferably, the reaction is conducted under low water conditions and the reaction medium contains from 0.1 to 4.1 wt. % water, e.g., from 0.1 to 3.1 wt. % or from 0.5 to 2.8 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The following amounts are based on the total weight of the reaction medium. The ranges disclosed in this application include the endpoints, subranges and individual values.

The concentration of acetic acid in the reaction medium is generally more than 30 wt. %, e.g. more than 40 wt. % or more than 50 wt. %.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm.

To control the exothermic carbonylation reaction, the reactor may have a sufficient cooling system. This reduces the need to recycle the liquid stream to provide the necessary cooling for the reactor. In one embodiment, there may be a pump around loop 103 for cooling the reactor. Pump around loop 103 operates to cool reaction medium by indirect contact with a coolant. Suitable pump around loops are described in U.S. Pat. No. 8,530,696, which is incorporated herein by reference in their entirety. In one embodiment, the heat of the reaction in the pump around reactor 103 may be recovered by the steam generator.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 105 to prevent buildup of gaseous by-products and to maintain a set carbon monoxide partial pressure at a given total reactor pressure. The temperature of the reactor may be controlled and the carbon monoxide feed is introduced at a rate sufficient to maintain the desired total reactor pressure. Stream 113 comprising the liquid reaction medium exits reactor 105.

The acetic acid production system preferably includes separation system 108 employed to recover the acetic acid and recycle metal catalyst, methyl iodide, methyl acetate, and other system components within the process. One or more of the recycle streams may be combined prior to being introduced into the reactor. The separation system also preferably controls water and acetic acid content in the carbonylation reactor, as well as throughout the system, and facilitates permanganate reducing compound ("PRC") removal. PRC's may include acetaldehyde, acetone, methyl ethyl ketone, butylaldehyde, crotonaldehyde, 2-ethyl crotonaldehyde, 2-ethyl butyraldehyde, and the aldol condensation products thereof.

The reaction medium is drawn off from the carbonylation reactor 105 at a rate sufficient to maintain a constant level therein and is provided to flasher 110 via stream 113. The flash separation may be carried out at a temperature from 80° C. to 200° C., under an absolute pressure from 1 to 10 atm. The reaction medium is separated in a flash separation step to obtain a vapor product stream 112 comprising acetic acid and liquid recycle 111 comprising a catalyst-containing solution. The catalyst-containing solution may be predominantly acetic acid containing the rhodium and the iodide salt along with lesser quantities of methyl acetate, methyl iodide, and water and is recycled to the reactor, as discussed above. Prior to returning liquid recycle to the reactor, a slip stream may pass through a corrosion metal removal bed, such as an ion exchange bed, to remove any entrained corrosion metals as described in U.S. Pat. No. 5,731,252, which is incorporated herein by reference in their entirety. Also, the corrosion metal removal bed may be used to remove nitrogen compounds, such as amines, as described in U.S. Pat. No. 8,697,908, which is incorporated herein by reference in their entirety.

In addition to acetic acid, vapor product stream 112 also comprises methyl iodide, methyl acetate, water, PRC's and other iodide compounds. Dissolved gases exiting reactor 105 and entering flasher 110 comprise a portion of the carbon monoxide and may also contain gaseous by-products such as methane, hydrogen, and carbon dioxide. Such dissolved gases exit flasher 110 as part of the vapor product stream 112. In one embodiment, carbon monoxide in gaseous purge stream 106 may be fed to base of flasher 110 to enhance rhodium stability.

Condensing of Vapor Product Stream

As shown in FIGS. 1 and 2, vapor product stream 112 is split into a first portion 140 and a second portion 141. These portions are aliquots of the vapor product stream. The first portion 140 is condensed by heat exchanger 142 to form a liquid stream 143 and a vapor stream 144.

In one embodiment, vapor product stream 112 that is condensed as first portion 140 may be from 1 to 50% of vapor product stream 112, e.g., preferably from 5 to 40% or more preferably from 10 to 35%. First portion 140 is cooled with a heat exchanger 142 to a temperature from 20° C. to 100° C., e.g., 20° C. to 70° C. or more preferably 20° C. to 50° C.

Vapor product stream 112 that is not condensed and fed to first column 120 as second portion 141 may be from 50 to 99% of the vapor product stream, e.g., preferably from 60 to 95% or more preferably from 65 to 90%.

As shown in FIG. 1, once cooled, at least 10% of liquid stream 143 may be fed to first column 120. In one preferred embodiment, at least 25%, e.g., at least 50%, at least 75% or at least 90% may be fed to first column 120. The remaining portion of liquid stream 143 not fed to first column 120 may be preferably fed to second column 125 or less preferably fed to reactor 105 via optional line 145. To avoid recycling acetic acid to reactor 105, more acetic acid from liquid stream 143 may be fed to first column 120 and/or second column 125 than is returned to reactor 105. More preferably, to reduce the hydraulic load on first column 120, the entire portion of liquid stream 143 is introduced above the feed of second portion 141 to first column 120. As indicated in FIG. 1, in embodiments, liquid stream 143 is fed to first column 120 at a point above 141 but preferably below side stream 124 to prevent entrainment of components present in liquid stream 143 into side stream 124. In particular, rhodium catalyst entrained in vapor product stream 112 is prevented from entrainment into side stream 124 by locating liquid stream 143 below the level at which side stream 124 is removed from first column 120.

In another embodiment, as shown in FIG. 2, once cooled, at least 10% of liquid stream 143 may be fed to second column 125. In one preferred embodiment, at least 25%, e.g., at least 50%, at least 75% or at least 90% may be fed to second column 125. Because there may be low levels of entrained catalysts in vapor product stream 112, and because first column 120 may be skipped, it is desirable to eliminate entrained catalyst prior to vapor product stream 112 leaving flasher 110. In FIG. 2, to avoid sending entrained metal catalyst to second column 125, a scrubber section 150 is provided in the upper portion of flasher 110. A wash 151 may be added to scrubber section 150 to remove entrained metals. In embodiments, wash 151 may comprise one or more of streams 133, 136, and high boiling residue stream 121. Accordingly, in embodiments the process further comprises directing a bottom stream from the first column, a bottom stream from the second column, an overhead stream from the second column, or a combination thereof into the upper scrubber section in an amount sufficient to remove at least a portion of the catalyst entrained in the vapor product stream. In embodiments, the wash flow 151 sufficient to remove at least a portion of the catalyst entrained in the vapor product stream is from 1 wt % to 50 wt % of vapor product stream 112.

The remaining portion of liquid stream 143 not fed to second column 125 may be preferably fed to first column 120 or less preferably fed to reactor 105 via optional line 145. Importantly, in embodiments, the remaining portion of liquid stream 143 is not fed into an overhead decanter or other vessel associated with stream 133. Stream 143 includes a substantial amount of acetic acid. As described herein, stream 133 may be biphasically separated into a light aqueous phase and heavy methyl iodide phase prior to further purification and removal of PRC's. The acetic acid present in stream 143 may affect phase separation of stream 133 and thus, have a detrimental effect on the process.

Recovery of Acetic Acid

The distillation and recovery of acetic acid is not particularly limited for the purposes of the present disclosure. In contrast to previous methods that recover acetic acid from the vapor product stream, the processes disclosed herein recover acetic acid from both the vapor product stream and a liquid stream condensed from the vapor product stream that is enriched in acetic acid.

As shown in FIG. 1, second portion 141 of vapor product stream 112 is directed to a first column 120, also referred to as a light ends column, along with some or all of liquid stream 143. Distillation yields a low-boiling overhead vapor stream 122, a purified acetic acid product that preferably is removed via a side stream 124, and a high boiling residue stream 121. In one embodiment, low-boiling overhead vapor stream 122 may comprise from 40 to 80 wt. % water, methyl acetate, methyl iodide, and carbonyl impurities. Side stream 124 may comprise from 90 to 98 wt. % acetic acid, from 1 to 2.5 wt. % water, from 0.1 to 5 wt. % methyl iodide, and from 0.1 to 5 wt. % methyl acetate. Acetic acid removed via side stream 124 preferably is subjected to further purification, such as in a second column 125, also referred to as a drying column, and separates side stream 124 into overhead stream 126 comprised primarily of water and bottoms stream 127 comprised primarily of acetic acid. Overhead stream 126 may comprise 50 to 75 wt. % water. Methyl acetate and methyl iodide are also removed from the side stream and concentrated in the overhead stream. Drying column bottoms stream 127 preferably comprises or consists essentially of acetic acid. In preferred embodiments, drying column bottoms stream 127 comprises acetic acid in an amount greater than 90 wt. %, e.g., greater than 95 wt. % or greater than 98 wt. %. Drying column bottoms stream 127 may be further processed, e.g. by passing through an ion exchange resin, prior to being stored or transported for commercial use.

As shown in FIG. 2, second portion 141 of vapor product stream 112 is directed to first column 120. In this embodiment, first column 120 receives only a vapor feed. Distillation yields a low-boiling overhead vapor stream 122, a side stream 124 comprising acetic acid, and a high boiling residue stream 121. Side stream 124 is subjected to further purification, along with along with some or all of liquid stream 143, in second column 125. Second column 125 operates to separate side stream 124 and liquid stream 143 into overhead stream 126 comprised primarily of water, and bottoms stream 127 comprised primarily of acetic acid. In one embodiment, due to the enriched acetic acid concentration of liquid stream 143, as compared to vapor product stream 112, liquid stream 143 may be separated in second column without disrupting the column dynamics. Advantageously, an acetic acid product having the same purity may be recovered when liquid stream 143 is fed to second column 125.

In embodiments, vapor product stream 112 comprises acetic acid, methyl iodide, methyl acetate, water, acetaldehyde, and hydrogen iodide. In embodiments, vapor product stream 112 comprises acetic acid in an amount from 45 to 75 wt. %, methyl iodide in an amount from 20 to 50 wt. %, methyl acetate in an amount of less than or equal to 9 wt. %, and water in an amount of less than or equal to 15 wt. %, based on the total weight of the vapor product stream. In other embodiments, vapor product stream 112 comprises acetic acid in an amount from 45 to 75 wt. %, methyl iodide in an amount from 24 to less than 36 wt. %, methyl acetate in an amount of less than or equal to 9 wt. %, and water in an amount of less than or equal to 15 wt. %, based on the total weight of the vapor product stream. In embodiments, vapor product stream 112 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In still other embodiments, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts less than or equal to 0.01 wt. %. Vapor product stream 112 may comprise hydrogen iodide in an amount less than or equal to 1 wt. %, based on the total weight of the vapor product stream, e.g., less than or equal to 0.5 wt. %, or less than or equal to 0.1 wt. %. Vapor product stream 112 is preferably substantially free of, i.e., contains less than or equal to 0.0001 wt. %, propionic acid, based on the total weight of the vapor product stream.

However, as discussed above, vapor stream 112 may also include a substantial amount of rhodium catalyst via entrainment during the flash evaporation in flasher 110. Catalyst entrainment represents a significant cost due to the expense associated with rhodium catalyst. In addition, rhodium entrainment may lead to fouling and other issues downstream, as well as result in measurable concentrations of rhodium in the final acetic acid product. Accordingly, scrubber 150 and/or proper location of liquid stream 143 relative to vapor stream 141 and sidedraw stream 124 results in an unexpected improvement in the art.

Liquid recycle stream 111 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of less than or equal to 1 wt. % (e.g., from 0.0001 to 1 wt. % acetaldehyde); and hydrogen iodide in an amount of less than or equal to 0.5 wt. % (e.g., from 0.0001 to 0.5 wt. % hydrogen iodide).

Low-boiling overhead vapor stream 122 separated from first column 120 contains a reaction component, such as methyl iodide, methyl acetate, and water, and it is preferable to retain these reaction components within the process. Low-boiling overhead vapor stream 122 is condensed by a heat exchanger into stream 133, which may be recycled to reactor 105 and/or refluxed first column 120. An offgas component may be vented via line 132 from condensed low-boiling overhead vapor stream 124. In addition, there may be a process for removing carbonyl impurities, such as acetaldehyde, that deteriorate the quality of the acetic acid product and may be removed in suitable impurity removal columns, extractors, and absorbers as described in U.S. Pat. Nos. 6,143,930; 6,339,171; 7,223,883; 7,223,886; 7,884,237; 7,855,306; and US Pub. Nos. 2006/0011462 and 2011/0288333, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove acetaldehyde from the condensed low-boiling overhead vapor stream in stream 133 before returning the stream to the reactor. These impurities may also be referred to herein as PRC's, described herein.

Although not shown a portion of stream 133 may be condensed and biphasically separated into a light aqueous liquid phase and/or heavy liquid phase comprised mainly of methyl iodide, and then directed to acetaldehyde or PRC removal system to recover methyl iodide and methyl acetate, while removing acetaldehyde. As shown in Tables 1 and 2, the light liquid phase and/or heavy liquid phase separated from stream 133 may each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of stream 133, i.e., the light aqueous phase and/or heavy liquid phase fed to the acetaldehyde or PRC removal system may vary from 1% to 99% of the mass flow of either the light liquid phase and/or heavy liquid phase, e.g., from 1 to 50%, from 2 to 45%, from 5 to 40%, 5 to 30% or 5 to 20%. Also in some embodiments, a portion of both the light liquid phase and heavy liquid phase may be fed to the acetaldehyde or PRC removal system. The portion of the light liquid phase not fed to the acetaldehyde or PRC removal system may be refluxed to the first column 120 or recycled to the reactor 105, as described herein. The portion of the heavy liquid phase not fed to the acetaldehyde or PRC removal system may be recycled to the reactor 105. Although a portion of heavy liquid phase may be refluxed to the first column, it is more desirable to return the methyl iodide enriched heavy liquid phase to the reactor.

Although the specific compositions of light liquid phase may vary widely, some exemplary compositions are provided below in Table 1.

TABLE 1

Exemplary Light Liquid Phase from Light Ends Overhead

| Component | conc. (Wt. %) | conc. (Wt. %) | conc. (Wt. %) |
|---|---|---|---|
| Water | 40-80 | 50-75 | 70-75 |
| Methyl Acetate | 1-50 | 1-25 | 1-15 |
| Acetic Acid | 1-40 | 1-25 | 5-15 |
| PRC's | <5 | <3 | <1 |
| Methyl Iodide | <10 | <5 | <3 |

In embodiments, an overhead decanter from the first column 120 is arranged and constructed to maintain a low interface level to prevent an excess hold up of methyl iodide. Although the specific compositions of heavy liquid phase may vary widely, some exemplary compositions are provided below in Table 2.

TABLE 2

Exemplary Heavy Liquid Phase from Light Ends Overhead

| Component | conc. (Wt. %) | conc. (Wt. %) | conc. (Wt. %) |
|---|---|---|---|
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The distillation columns and other vessels of suitable for use include conventional distillation columns, e.g., a plate column, a packed column, and others. Plate columns may include a perforated plate column, bubble-cap column, Kittel tray column, uniflux tray, or a ripple tray column. The material of the distillation column is not limited and may include a glass, a metal, a ceramic, or other suitable material can be used. For a plate column, the theoretical number of plates is not particularly limited and depending on the species of the component to be separate, may depend on the component to be separated, and may include up to 50 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably about 100 to 160° C.

The material of each member or unit associated with the distillation system, including the columns, valves, condensers, receivers, pumps, reboilers, and internals, and various lines, each communicating to the distillation system may be suitable material such as glass, metal, ceramic, or combinations thereof, and is not particularly limited to a specific one. In embodiments, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloy include any alloy containing iron as a main component, e.g., a stainless steel that also comprises chromium, nickel, molybdenum and others. Suitable a nickel-based alloy include containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

In one embodiment, a portion of light liquid phase and/or heavy liquid phase is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase is treated in the PRC removal system, it may be desirable to return a portion the raffinate to either the distillation column or reactor. Also, for example, when light liquid phase is treated in the PRC removal system, it may be desirable to return a portion the raffinate to either the first column, overhead decanter, or reactor. In some embodiments, the extractant may be further distilled to remove water, which is returned to the one or more extraction stages. in which contains more methyl acetate and methyl iodide than light liquid phase, may also be recycled to reactor 105 and/or refluxed to first column 120.

Accordingly, the condensed low-boiling overhead vapor stream in stream 133 may be separated into an aqueous phase and an organic phase, and these phases may be recycled or refluxed as needed to maintain the concentrations in the reaction medium. Also, carbonyl impurities may be removed from these phases.

Similarly, overhead stream 126 from second column 125 contains a reaction component, such as methyl iodide, methyl acetate, and water, and it is preferable to retain these reaction components within the process. Overhead stream 126 is condensed by a heat exchanger into stream 136, which is recycled to reactor 105 and/or refluxed second column 125. An offgas component may be vented via line 135 from condensed low-boiling overhead vapor stream 126. Similar to the condensed low-boiling overhead vapor stream in stream 133, condensed overhead stream in stream 136 may also be separated into an aqueous phase and an organic phase, and these phases may be recycled or refluxed as needed to maintain the concentrations in the reaction medium.

To recover components, especially reaction components, from the vent stream, in particular lines 106, 132, 135, and 144, these lines may be fed to a scrubber that operates with cooled methanol and/or acetic acid to recover methyl acetate and methyl iodide that may be directly or indirectly recycled to the reactor. A suitable scrubber is described in U.S. Pat. No. 8,318,977, which is incorporated herein by reference in its entirety.

The distillation columns of according to the instant disclosure may be conventional distillation column, e.g., a plate column, a packed column, and others. The material of the distillation column is not limited and may include a glass, a metal, a ceramic, or other suitable material can be used. For a plate column, the theoretical number of plates may depend on the component to be separated, and may include up to 50 plates, e.g., from 5 to 50, or from 7 to 35.

Guard Bed

Carboxylic acid streams, e.g., acetic acid streams that are contaminated with a halides and/or corrosion metals may be contacted with the inventive ion exchange resin composition under a wide range of operating conditions. Preferably, the ion exchange resin composition is provided in a guard bed. The use of guard beds to purify contaminated carboxylic acid streams is well documented in the art, for example, U.S. Pat. Nos. 4,615,806; 5,653,853; 5,731,252; and 6,225,498, which are hereby incorporated by reference in their entireties. Generally, a contaminated liquid carboxylic acid stream is contacted with the ion exchange resin composition, which is preferably disposed in the guard bed. The halide contaminants, e.g., iodide contaminants, react with the metal to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

The pressure during the contacting step is limited only by the physical strength of the resin. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) and 118° C. (the boiling point of acetic acid). It is within the purview of those skilled in the art to determine analogous ranges for product streams comprising other carboxylic acid compounds. The temperature of the contacting step preferably is kept relatively low to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin degrading (via the mechanism of acid-catalyzed aromatic desulfonation) at temperatures of 150° C. Carboxylic acids having up to 5 carbon atoms, e.g., up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for halide removal.

The configuration of the guard bed within an acetic acid purification train may vary widely. For example, the guard bed may be configured after a drying column. Additionally or alternatively, the guard be may be configured after a heavy ends removal column or finishing column. Preferably the guard bed is configured in a position wherein the temperature acetic acid product stream is low, e.g., less than 120° C. or less than 100° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

In one embodiment, the flow rate through the guard bed ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

To avoid exhausting the resin with a purified acetic acid product that is high in total iodide concentration, in one embodiment the purified acetic acid product in bottoms stream 127 is contacted with a guard bed when total iodide concentration of the purified acetic acid product is less than 1 wppm. Total iodide concentration includes iodide from both organic sources, $C_1$ to $C_{14}$ alkyl iodides, and inorganic sources, such as hydrogen iodide. A purified acetic acid composition is obtained as a result of the guard bed treatment. The purified acetic acid composition, in one embodiment, comprises less than 100 wppb, iodides, e.g., less than 90 wppb, less than 50 wppb, or less than 25 wppb. In one embodiment, the purified acetic acid composition comprises less than 100 wppb corrosion metals, e.g., less than 750 wppb, less than 500 wppb, or less than 250 wppb. In terms of ranges, the purified acetic acid composition may comprise from 0 to 100 wppb iodides, e.g., from 1 to 50 wppb; and/or from 0 to 1000 wppb corrosion metals, e.g., from 1 to 500 wppb. In other embodiments, the guard bed removes at least 25 wt. % of the iodides from the crude acetic acid product, e.g., at least 50 wt. % or at least 75 wt. %. In one embodiment, the guard bed removes at least 25 wt. % of the corrosion metals from the crude acetic acid product, e.g., at least 50 wt. % or at least 75 wt. %.

In embodiments, the process for producing acetic acid further includes introducing a lithium compound into the reactor to maintain the concentration of lithium acetate in an amount from 0.3 to 0.7 wt % in the reaction medium. In embodiments, an amount of the lithium compound is introduced into the reactor to maintain the concentration of hydrogen iodide in an amount from 0.1 to 1.3 wt % in the reaction medium. In embodiments, the concentration of the rhodium catalyst is maintained in an amount from 300 to 3000 wppm in the reaction medium, the concentration of water is maintained in amount from 0.1 to 4.1 wt % in the reaction medium, and the concentration of methyl acetate is maintained from 0.6 to 4.1 wt % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

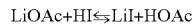

$$\text{LiOAc} + \text{HI} \leftrightharpoons \text{LiI} + \text{HOAc} \qquad \text{(I)}$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid—base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at less than or equal to 0.7 wt. %, or less than or equal to 0.65 wt. %, or less than or equal to 0.6 wt. %, or less than or equal to 0.55 wt. %, when determined according to perchloric acid titration to a potentiometric endpoint.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % results in a lack of control over hydrogen iodide concentrations within the reaction medium.

In embodiments, the lithium compound may be introduced continuously or intermittently into the reaction medium. In embodiments, the lithium compound is introduced during reactor start up. In embodiments, the lithium compound is introduced intermittently to replace entrainment losses.

A series of experiments conducted to demonstrate the promotional effect of lithium acetate in the carbonylation reactor and to determine the effect of lithium acetate on the methyl iodide oxidative addition to the rhodium complex, $Li[RhI_2(CO)_2]$ confirmed the promotional effect of lithium acetate on reaction rates. A linear increase of reaction rates correlated to increasing lithium acetate concentrations was observed. This correlation was indicative of first order promotional effects of reaction between methyl iodide and $Li[RhI_2(CO)_2]$. These experiments further showed a non-zero intercept, confirming that lithium acetate is not required for the MeI—Rh(I) reaction to occur, but the lithium acetate does give considerable promotional effect even at low concentrations.

In embodiments, the process may further comprise maintaining a butyl acetate concentration in the acetic acid product at 10 wppm or less without directly removing butyl acetate from the product acetic acid. In embodiments, the butyl acetate concentration in the final acetic acid product may be maintained below 10 ppm by removing acetaldehyde from the reaction medium, e.g., removing acetaldehyde from a stream derived from the reaction medium, and/or by controlling the reaction temperature, and/or the hydrogen partial pressure, and/or the metal catalyst concentration in the reaction medium. In embodiments, the butyl acetate concentration in the final acetic acid product is maintained by controlling one or more of the carbonylation reaction temperature from 150° C. to 250° C., the hydrogen partial pressure in the carbonylation reactor at from 0.3 to 2 atm, the rhodium metal catalyst concentration in the reaction medium at from 100 to 3000 wppm, based on the total weight of the reaction medium, and/or the acetaldehyde concentration in the reaction medium at 1500 ppm or less.

In embodiments, the acetic acid product formed according to embodiments of the process disclosed herein has a butyl acetate concentration of less than or equal to 10 wppm, or less than or equal to 9 wppm, or less than or equal to 8 wppm, or less than or equal to 6 wppm, or less than or equal to 2 wppm, based on the total weight of the acetic acid product. In embodiments, the acetic acid product is substantially free of butyl acetate, i.e., a butyl acetate concentration of less than 0.05 wppm or is non-detectable by detection means known in the art. In embodiments, the acetic acid product may also have a propionic acid concentration of less than 250 wppm, or less than 225 ppm, or less than 200 wppm.

In embodiments, the butyl acetate concentration in the acetic acid product may be controlled by controlling the concentration of acetaldehyde in the reaction medium. While not wishing to be bound by theory, butyl acetate is thought to be a by-product caused by aldol condensation of acetaldehyde. Applicant has discovered that by maintaining the acetaldehyde concentration in the reaction medium at less than 1500 wppm, the concentration of butyl acetate in the final acetic acid product may be controlled below 10 wppm. In embodiments, the acetaldehyde concentration in the reaction medium is maintained at less than or equal to 1500 wppm, or less than or equal to 900 wppm, or less than or equal to 500 wppm, or less than or equal to 400 wppm, based on the total weight of the reaction medium.

In embodiments, the butyl acetate concentration in the acetic acid product may be controlled by controlling the reaction temperature of the carbonylation reactor at a temperature greater than or equal to 150° C., or 180° C., and less than or equal to 250° C., or 225° C.; and/or the hydrogen partial pressure in the carbonylation reactor may be controlled at greater than or equal to 0.3 atm, or 0.35 atm, or 0.4 atm, or 0.5 atm, and less than or equal to 2 atm, or 1.5 atm, or 1 atm.

While relatively high hydrogen partial pressure results in improved reaction rates, selectivity, improved catalyst activity, and reduced temperatures, applicant has discovered that as hydrogen partial pressure is increased, impurity production is also increased, including butyl acetate.

In embodiments, the hydrogen partial pressure may be controlled by modifying the amount of hydrogen present in the carbon monoxide source and/or by increasing or decreasing the reactor vent flows to obtain the desired hydrogen partial pressure within the carbonylation reactor.

A series of experiments were conducted to demonstrate the effect of hydrogen partial pressure and acetaldehyde concentration in the reaction medium on the concentration of butyl acetate in the final acetic acid product. These experiments confirmed a correlation between reduced butyl acetated concentrations in the final acetic acid product, and relatively low acetaldehyde concentrations in the reaction medium and/or relatively low hydrogen partial pressures in the carbonylation reactor. Experiments in which the acetaldehyde concentration in the reactor was maintained below 1500 ppm and the reactor hydrogen partial pressure maintained below 0.6 atm resulted in butyl acetate levels below 10 wppm in the final acetic acid product. Other experiments showed an acetaldehyde concentration in the reactor below 1500 wppm and a reactor hydrogen partial pressure of 0.46 atm resulted in a butyl acetate concentration of less than 8 wppm in the final acetic acid product. Similar conditions in which the hydrogen partial pressure was 0.30 atm resulted in butyl acetate levels below 6 wppm, and hydrogen partial pressures of 0.60 atm resulted in butyl acetate concentrations below 0.2 wppm in the final acetic acid product. However, comparative experiments in which the hydrogen partial pressure was 0.4 and 0.3 respectively, but in the absence of an aldehyde removal system such that the acetaldehyde concentrations in the reactor exceeded 1500 wppm, resulted in a final acetic acid product having butyl acetate levels of 13 wppm and 16 wppm respectively.

Applicant has further discovered that the concentration of propionic acid in the final acetic acid product may be affected by the concentration butyl acetate in the acetic acid product. Accordingly, by controlling the butyl acetate concentration in the final acetic acid product to 10 wppm or less, the concentration of propionic acid in the final acetic acid product may be controlled to less than 250 wppm, or less than 225 ppm, or less than 200 wppm. Likewise, by controlling the ethanol content in the reactor feed, which may be present as an impurity in the methanol source, the propionic acid and butyl acetate concentrations in the final acetic acid product may also be controlled. In embodiments, the concentration of ethanol in the methanol feed to the carbonylation reactor is controlled to less than or equal to 150 wppm. In embodiments, if present, the ethanol concentration in the methanol feed to the reactor is less than or equal to 100 wppm, or 50 wppm, or 25 wppm.

Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the concentration of ethyl iodide in the reaction medium is maintained/controlled to be less than or equal to 750 wppm, or less than or equal to 650 wppm, or less than or equal to 550 wppm, or less than or equal to 450 wppm, or less than or equal to 350 wppm. In alternative embodiments, the concentration of ethyl iodide in the reaction medium is maintained/controlled at greater than or equal to 1 wppm, or 5 wppm, or 10 wppm, or 20 wppm, or 25 wppm, and less than or equal to 650 wppm, or 550 wppm, or 450 wppm, or 350 wppm.

In embodiments, the propionic acid concentration in the acetic acid product may further be maintained below 250 wppm by maintaining the ethyl iodide concentration in the reaction medium at less than or equal to 750 wppm without removing propionic acid from the acetic acid product.

In embodiments, the ethyl iodide concentration in the reaction medium and propionic acid in the acetic acid product may be present in a weight ratio from 3:1 to 1:2, or from 5:2 to 1:2, or from 2:1 to 1:2. In embodiments, the acetaldehyde:ethyl iodide concentration in the reaction medium is maintained at a weight ratio from 2:1 to 20:1, or from 15:1 to 2:1, or from 9:1 to 2:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

A series of experiments conducted to determine the effect of acetaldehyde and other reaction conditions on the formation of ethyl indicated a relationship between acetaldehyde concentration and ethyl iodide concentration in the reaction medium, as well as relationships between the reactor concentration of ethyl iodide and the concentration of propionic acid in the final acetic acid product. In general, an ethyl iodide concentration of less than 750 wppm and an acetaldehyde concentration of less than 1500 wppm in the reaction medium resulted in propionic acid concentrations of less than 250 wppm in the acetic acid product.

As is evident from the figures and text presented above, a variety of embodiments are contemplated:

E1. A process for producing acetic acid comprising:
   carbonylating at least one reactant selected from the group consisting of methanol, dimethyl ether, methyl acetate, and mixtures thereof, in the presence of 0.1 to 14 wt. % water, a metal catalyst, methyl iodide and iodide salt to form a reaction medium in a reactor;
   separating the reaction medium into a liquid recycle and a vapor product stream including acetic acid, methyl iodide, methyl acetate and water;
   condensing a first portion of the vapor product stream to form a liquid stream; feeding a second portion of the vapor product stream to a first column;
   feeding at least a portion of the liquid stream to the first column; and withdrawing a side stream from the first column comprising an acetic acid product.

E2. The process according to embodiment E1, wherein 1 to 50 wt. % of the vapor product stream is condensed to form the liquid stream, and wherein 50 to 99 wt. % of the vapor product stream is fed to the first column.

E3. The process according to embodiment E1 or E2, wherein at least 10 wt % of the liquid stream is fed to the first column.

E4. The process according to any one of embodiments E1 to E3, further comprising:
   feeding the side stream comprising the acetic acid product to a second column to obtain an acetic acid purified product.

E5. The process according to embodiment E4, wherein at least a portion of the liquid stream is introduced into the second column.

E6. The process according to any one of embodiments E1 to E5, wherein the reaction is conducted while maintaining the reaction medium at concentrations of 1 to 25 wt. % iodide salt, 1 to 25 wt. % methyl iodide, 0.5 to 30 wt. % methyl acetate, and 0.1 to 14 wt. % water.

E7. The process according to any one of embodiments E1 to E6, wherein the reactor further comprises a cooling unit.

E8. The process according to any one of embodiments E1 to E7, wherein the liquid stream comprises from 65 to 95 wt. % acetic acid.

E9. The process according to any one of embodiments E1 to E8, wherein the liquid stream is enriched in acetic acid compared to the second portion of the vapor product stream.

E10. The process according to any one of embodiments E1 to E9, wherein the liquid stream is fed to the first column above the feed of the second portion of the vapor product stream.

E11. The process according to any one of embodiments E1 to E10, wherein the liquid stream is fed to the first column below the point at which the side stream comprising the acetic acid product is withdrawn from the first column.

E12. The process according to any one of embodiments E1 to E11, wherein carbon monoxide efficiency in the reactor is maintained above 90%.

E13. A process for producing acetic acid comprising:
carbonylating at least one reactant selected from the group consisting of methanol, dimethyl ether, methyl acetate, and mixtures thereof in the presence of 0.1 to 14 wt. % water, a metal catalyst, methyl iodide and iodide salt to form a reaction medium in a reactor;
separating the reaction medium into a liquid recycle and a vapor product stream including acetic acid, methyl iodide, methyl acetate and water in a flash vessel having an optional upper scrubbing section;
condensing a first portion of the vapor product stream to form a liquid product stream; feeding a second portion of the vapor product stream to a first column;
withdrawing a side stream comprising an acetic acid product from the first column; feeding the side stream to a second column;
feeding at least a portion of the liquid product stream to the second column; and obtaining an acetic acid purified product from the second column.

E14. The process according to embodiment E13, wherein 1 to 50 wt % of the vapor product stream is condensed to form the liquid stream and wherein 50 to 99 wt % of the vapor product stream is fed as the second portion to the first column.

E15. The process according to embodiments E13 or E14, wherein at least 10 wt % of the liquid stream is fed to the second column.

E16. The process according to any one of embodiments E13 to E15, wherein at least a portion of the liquid stream is introduced into the first column.

E17. The process according to any one of embodiments E13 to E16, further comprising directing a bottom stream from the first column, a bottom stream from the second column, an overhead stream from the second column, or a combination thereof into the upper scrubber section in an amount sufficient to remove at least a portion of the catalyst entrained in the vapor product stream.

E18. The process according to any one of embodiments E13 to E17, wherein the liquid stream comprises from 65 to 95 wt. % acetic acid.

E19. The process according to any one of embodiments E13 to E18, wherein the liquid stream comprises an amount equal to or greater than the amount of acetic acid in the side stream.

E20. The process according to any one of embodiments E13 to E19, wherein the liquid stream is fed to the second column above the feed of the side stream.

E21. The process according to any one of embodiments E1 to E20, wherein the water concentration in the reaction medium is controlled from 0.1 to 5 wt %, based on the total amount of reaction medium present.

E22. The process according to any one of embodiments E1 to E21, further comprising introducing a lithium compound selected from the group consisting of lithium acetate, lithium carboxylates, lithium carbonates, lithium hydroxide, and mixtures thereof into the reactor to maintain the concentration of lithium acetate from 0.3 to 0.7 wt % in the reaction medium.

E23. The process according to embodiment E22, further comprising:
maintaining the hydrogen iodide concentration from 0.1 to 1.3 wt % in the reaction medium;
maintaining the rhodium catalyst concentration from 300 and 3000 wppm in the reaction medium;
maintaining the water concentration from 0.1 to 4.1 wt % in the reaction medium;
maintaining the methyl acetate concentration from 0.6 to 4.1 wt % in the reaction medium; or a combination thereof.

E24. The process according to any one of embodiments E1 to E23, further comprising controlling a butyl acetate concentration in the acetic acid product at 10 wppm or less without directly removing butyl acetate from the acetic acid product.

E25. The process according to embodiment E24, wherein the butyl acetate concentration is controlled by maintaining an acetaldehyde concentration at 1500 ppm or less in the reaction medium.

E26. The process according to embodiment E24 or E25, wherein the butyl acetate concentration is controlled by controlling a temperature in the reactor from 150 to 250° C.

E27. The process according to any one of embodiments E25 to E26, wherein the butyl acetate concentration is controlled by controlling a hydrogen partial pressure in the reactor from 0.3 to 2 atm.

E28. The process according to any one of embodiments E24 to E27, wherein the butyl acetate concentration is controlled by controlling a rhodium catalyst concentration from 100 to 3000 wppm in the reaction medium.

E29. The process according to any one of embodiments E1 to E28, further comprising controlling an ethyl iodide concentration in the reaction medium at less than or equal to 750 wppm.

E30. The process according to embodiment E29, wherein the propionic acid concentration in the product acetic acid is less than 250 wppm, without directly removing propionic acid from the product acetic acid.

E31. The process according to embodiment E29 or E30, wherein ethyl iodide in the reaction medium and propionic acid in the acetic acid product are present in a weight ratio from 3:1 to 1:2;

E32. The process according to any one of embodiments E29 to E31, wherein acetaldehyde and ethyl iodide are present in the reaction medium in a weight ratio from 2:1 to 20:1;

E33. The process according to any one of embodiments E29 to E32, wherein an ethanol concentration in the methanol feed into the reactor is less than 150 wppm; or a combination thereof E34. The process according to any one of embodiments E29 to E33, wherein the ethyl iodide concentration in the reaction medium is controlled by adjusting at least one of a hydrogen partial pressure in the carbonylation reactor, a methyl acetate concentration in the reaction medium, and a methyl iodide concentration in the reaction medium.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

What is claimed is:

1. A process for producing acetic acid comprising:
carbonylating at least one reactant selected from the group consisting of methanol, dimethyl ether, methyl acetate, and mixtures thereof, in the presence of 0.1 to 14 wt. % water, a metal catalyst, methyl iodide and iodide salt to form a reaction medium in a reactor;
separating the reaction medium into a liquid recycle and a vapor product stream including acetic acid, methyl iodide, methyl acetate and water;
condensing a first portion of the vapor product stream to form a liquid stream; feeding a second portion of the vapor product stream to a first column;
feeding at least a portion of the liquid stream to the first column; and
withdrawing a side stream from the first column comprising an acetic acid product,
wherein the liquid stream is fed to the first column above the feed of the second portion of the vapor product stream and wherein the liquid stream is fed to the first column below the point at which the side stream comprising the acetic acid product is withdrawn from the first column.

2. The process of claim 1, wherein 1 to 50 wt. % of the vapor product stream is condensed to form the liquid stream, and wherein 50 to 99 wt. % of the vapor product stream is fed to the first column.

3. The process of claim 1, wherein at least 10 wt % of the liquid stream is fed to the first column.

4. The process of claim 1, further comprising:
feeding the side stream comprising the acetic acid product to a second column to obtain an acetic acid purified product.

5. The process of claim 4, wherein at least a portion of the liquid stream is introduced into the second column.

6. The process of claim 1, wherein the reaction is conducted while maintaining the reaction medium at concentrations of 1 to 25 wt. % iodide salt, 1 to 25 wt. % methyl iodide, 0.5 to 30 wt. % methyl acetate, and 0.1 to 14 wt. % water.

7. The process of claim 1, wherein the reactor further comprises a cooling unit.

8. The process of claim 1, wherein the liquid stream comprises from 65 to 95 wt. % acetic acid.

9. The process of claim 1, wherein the liquid stream is enriched in acetic acid compared to the second portion of the vapor product stream.

10. The process of claim 1, wherein carbon monoxide efficiency in the reactor is maintained above 90%.

11. A process for producing acetic acid comprising:
carbonylating at least one reactant selected from the group consisting of methanol, dimethyl ether, methyl acetate, and mixtures thereof in the presence of 0.1 to 14 wt. % water, a metal catalyst, methyl iodide and iodide salt to form a reaction medium in a reactor;
separating the reaction medium into a liquid recycle and a vapor product stream including acetic acid, methyl iodide, methyl acetate and water in a flash vessel having an optional upper scrubbing section;
condensing a first portion of the vapor product stream to form a liquid product stream;
feeding a second portion of the vapor product stream to a first column;
withdrawing a side stream comprising an acetic acid product from the first column;
feeding the side stream to a second column;
feeding at least a portion of the liquid product stream to the second column; and
obtaining an acetic acid purified product from the second column,
wherein the liquid stream is fed to the second column above the feed of the side stream.

12. The process of claim 11, wherein 1 to 50 wt % of the vapor product stream is condensed to form the liquid stream and wherein 50 to 99 wt % of the vapor product stream is fed as the second portion to the first column.

13. The process of claim 11, wherein at least 10 wt % of the liquid stream is fed to the second column.

14. The process of claim 11, wherein at least a portion of the liquid stream is introduced into the first column.

15. The process of claim 11, further comprising directing a bottom stream from the first column, a bottom stream from the second column, an overhead stream from the second column, or a combination thereof into the upper scrubbing section in an amount sufficient to remove at least a portion of the catalyst entrained in the vapor product stream.

16. The process of claim 11, wherein the liquid stream comprises from 65 to 95 wt. % acetic acid.

17. The process of claim 11, wherein the liquid stream comprises an amount equal to or greater than the amount of acetic acid in the side stream.

* * * * *